US006025161A

United States Patent [19]
Davie et al.

[11] Patent Number: 6,025,161
[45] Date of Patent: *Feb. 15, 2000

[54] DNA SEQUENCES EXPRESSING MAMMALIAN $\alpha_1$-ANTITRYPSIN

[75] Inventors: Earl W. Davie, Bellevue; Kotoku Kurachi, Seattle, both of Wash.; Savio L. C. Woo; Chandra Thirumalachary, both of Houston, Tex.

[73] Assignee: Washington Research Foundation, Seattle, Wash.

[ * ] Notice: This patent is subject to a terminal disclaimer.

[21] Appl. No.: 09/009,581

[22] Filed: Jan. 20, 1998

Related U.S. Application Data

[62] Division of application No. 08/479,545, Jun. 7, 1995, Pat. No. 5,736,379, which is a continuation of application No. 08/361,689, Nov. 22, 1994, abandoned, which is a continuation of application No. 08/086,442, Jul. 2, 1993, Pat. No. 5,399,684, which is a continuation of application No. 07/979,556, Nov. 18, 1992, abandoned, which is a continuation of application No. 07/666,450, Mar. 11, 1991, abandoned, which is a continuation of application No. 07/398,288, Aug. 22, 1989, abandoned, which is a continuation of application No. 07/246,912, Sep. 16, 1988, abandoned, which is a continuation of application No. 07/133,190, Dec. 15, 1987, abandoned, which is a continuation of application No. 07/022,543, Mar. 3, 1987, abandoned, which is a continuation of application No. 06/638,980, Feb. 7, 1984, abandoned, which is a continuation of application No. 06/380,810, May 20, 1982, abandoned.

[51] Int. Cl.[7] ................................................... C12P 21/02
[52] U.S. Cl. ......................................... 435/69.2; 435/69.1
[58] Field of Search .................. 435/69.1, 252.3–252.35, 435/69.2; 536/23.5

[56] References Cited

U.S. PATENT DOCUMENTS

| | | | |
|---|---|---|---|
| 4,530,901 | 7/1985 | Weissman | 435/69.51 |
| 5,399,684 | 3/1995 | Davie et al. | 536/23.5 |
| 5,736,379 | 4/1998 | Davie et al. | 435/252.3 |

OTHER PUBLICATIONS

Wallace et al., "Hybridization of synthetic oligodeoxyribonucleotides to $\phi_x$ 174 DNA: the effect of base pair mismatch," *Nucleic Acids Res.* 6:3543–3557, 1979.

Suggs et al., "Use of synthetic oligonucleotides as hybridization probes: Isolation of cloned cDNA sequences for human $\beta_s$-microglobulin," *Proc. Natl. Acad. Sci. USA* 78:6617, 1981.

Wilson et al., "Isolation of human alpha–1 anti trypsin mRNA from liver tissue for molecular cloning" in *J. Supramol. Struct. Cell. Biochem.* (Suppl. 5) 1981, 421, Abstract No. 1133, presented at the ICN–University of California at Los Angeles, Mar. 15–20, 1981.

Kurachi et al., "Cloning and sequence of cDNA coding for a lpha–1–antitrypsin", *Proc. Nat. Acad. Sci. USA* 78:6826, 1982/1981.

Clissold et al., "Molecular Cloning of cDNA sequences transcribed from mouse liver endoplasmic reticulum poly (A)mRNA", *Biol. Abstr.* 73:60806 (1982. of Gene 15:225–235, 1981.

Houghton et al., "The amino–terminal sequence of human fibroblast interferon as deduced from reverse transcripts obtained using synthetic oligonucleotide primer", *Nucl. Acids. Res.* 8:1913, 1980.

Morii et al., "Human alph–1–antitrypsin, Characterization and N– and C– terminal sequences", *J. Biochem.* 83:269, 1978.

Roberts et al., "A general method for maximizing the expression of a cloned gene", *Proc. Natl. Acad. Sci. USA* 76:760, 1979.

Goeddel et al., "Synthesis of human fibroblast interferon by *E. coli,*" *Nucleic Acids Res.* 8:4057, 1980.

Woo et al., "The human alpha–1–antitrypsin gene: its sequence homology and structural comparison with the chicken ovalbumin gene", *Chem. Abstr.* 98:120615Z, 1983, of UCLA Symp., *Mol. Cell Biol.* 26(Gene Regul.):55–64, 1982.

Shochat et al., "Primary Structure of Human $\alpha_1$–Protease Inhibitor," *J. Biol. Chem.* 253:5630–5634, 1978.

Carrell et al., "Carboxy terminal fragment of Human $\alpha$–1–antitrypsin from hydroxylamine cleavage: homology with antithrombin III," *Biochem. Biophys. Res. Commun.* 91:1032–1037, 1979.

Mega et al., "Studies on the Oligosaccharide Chains of Human $\alpha_1$–Protease Inhibitor," *P.J. Biol. Chem.* 255:4057–4061, 1980.

Crawford, "Purification and Properties of Normal Human $\alpha_1$–Antitrypsin," *Arch. Biochem. Biophys.* 156:215–222, 1973.

Chandra et al., *Biochem. Biophys. Res. Commun.* 103:751–758, 1981.

Woo et al., "Induction and cloning of the $\alpha_{1-antitrypsin\ gene}$," *Federation Proceedings* 40(6):1754, Abstract No. 1240, May 1, 1981.

Davie, E.W., "Cloning of fibrinogen, prothrombin, and $\alpha_1$–antitrypsin," The Harvey Lectures, Series 77, Academic Press, New York, pp. 1–21, 1983.

Kurachi et al., "Isolation and characterization of a cDNA clone coding for $\alpha_1$–antitrypsin," Abstract No. 0255, Eighth International Conference on Thrombosis and Haemostatis, Jul. 14, 1981.

Woo et al., "The human alpha–1–antitrypsin gene and pulmonary emphysema," Abstract No. 7061, Twenty–first Annual Meeting of the American Society for Cell Biology, Nov. 9–13, 1981.

(List continued on next page.)

*Primary Examiner*—James Martinell
*Attorney, Agent, or Firm*—Christensen O'Connor Johnson & Kindess PLLC

[57] ABSTRACT

DNA sequences to mammalian $\alpha_1$-antitrypsin are provided which can be used for expression of mammalian $\alpha_1$-antitrypsin.

This work was supported in part by grants HL16919 and HL27509 from the National Institutes of Health.

2 Claims, 11 Drawing Sheets

OTHER PUBLICATIONS

Davie et al., "The structure and cloning of the $\alpha_1$ antitrypsin gene," *Protein, Nucleic Acid and Enzyme* 27(12):1805–1809, 1982, based on a lecture in Nov. 1981.

Kurachi et al., "Cloning and nucleotide sequences of cDNA and genomic DNA coding for $\alpha_1$–antitrypsin," *Fed. Proc.* 41:517, Abstract No. 1446, Apr. 15–23, 1982.

Colten, H.R., et al., "Genetics and biosynthesis of complement proteins," *New Engl. J. of Med.* 304:653–456, 1981.

Colten, H.R., et al., "Synthesis and secretion of complement proteins by macrophages," *Annals New York Academy of Sciences* 332:482–490, 1979.

Reid, K.B.M., et al., "The proteolytic activation systems of complement," *Ann. Rev. Biochem*, 50:433–464, 1981.

```
5'
G G G G G G G G G G G G G G A G T G A A T C G A C A
-24
         Met Pro Ser Ser Val Ser Trp Gly Ile Leu
         ATG CCG TCT TCT GTC TCT TGG GGC ATC CTC
+1           -20                       -10        
                          10              20              30

Leu Ala Gly Leu Cys Cys Leu Val Pro
CTG GCA GGC CTG TGC TGC CTG GTC CCT
            40              50              60

Val Ser Leu Ala Glu Asp Pro Gln Gly Asp
GTC TCC CTG GCT GAG GAT CCC CAG GGA GAT
    -1    1              70              80              90

Ala Ala Gln Lys Thr Asp Thr Ser His His
GCT GCC CAG AAG ACA GAT ACA TCC CAC CAT
            10              100             110             120
```

FIGURE 1A

```
                 20                                         30
Asp Gln Asp His Pro Thr Phe Asn Lys Ile   Thr Pro Asn Leu Ala Glu Phe Ala Phe Ser
GAT CAG GAT CAC CCA ACC TTC AAC AAG ATC   ACC CCC AAC TTG GCT GAG TTC GCC TTC AGC
             130         140         150               160         170         180

40                                         50
Leu Tyr Arg Gln Leu Ala His Gln Ser Asn   Ser Thr Asn Ile Phe Phe Ser Pro Val Ser
CTA TAC CGC CAG CTG GCA CAC CAG TCC AAC   AGC ACC AAT ATC TTC TTC TCC CCA GTG AGC
             190         200         210               220         230         240
```

FIGURE 1B

```
      60                    70                    80                    90
Ile Ala Thr Ala Phe Ala Met Leu Ser Leu   Gly Thr Lys Ala Asp Thr His Asp Glu Ile   Leu Glu Gly Leu Asn Phe Asn Leu Thr Glu   Ile Pro Glu Ala Gln Ile His Glu Gly Phe
ATC GCT ACA GCC TTT GCA ATG CTC TCC CTG   GGA ACC AAG GCT GAC ACT CAC GAT GAA ATC   CTG GAG GGC CTG AAT TTC AAC CTT CAC GGA G  ATT CCG GAG GCT CAG ATC CAT GAA GGC TTC
                    250                    260                    270                    280                    290                    300                    310                    320                    330                    340                    350                    360
```

FIGURE 1C

```
Gln  Glu  Leu  Leu  Arg  Thr  Leu  Asn  Gln  Pro
CAG  GAA  CTC  CTC  CGT  ACC  CTC  AAC  CAG  CCA
    100                      380                  390
                370

Asp  Ser  Gln  Leu  Gln  Leu  Thr  Thr  Gly  Asn
GAC  AGC  CAG  CTC  CAG  CTG  ACC  ACC  GGC  AAT
    110                      410                  420
                400

Gly  Leu  Phe  Leu  Ser  Glu  Gly  Leu  Lys  Leu
GGC  CTG  TTC  CTC  AGC  GAG  GGC  CTG  AAG  CTA
    120                      440                  450
                430

Val  Asp  Lys  Phe  Leu  Glu  Asp  Val  Lys  Lys
GTG  GAT  AAG  TTT  TTG  GAG  GAT  GTT  AAA  AAG
    130                      470                  480
                460
```

FIGURE 1D

```
        140
Leu Tyr His Ser Glu Ala Phe Thr Val Asn
T T G T A C C A C T C A G A A G C C T T C A C T G T C A A C
                490                 500                 510

150
Phe Gly Asp Thr Thr Glu Glu Ala Lys Lys Gln
T T C G G G G A C A C C G A A G A G G C C A A G A A A C A G
                520                 530                 540

160
Ile Asn Asp Tyr Val Glu Lys Gly Thr Gln
A T C A A C G A T T A C G T G G A G A A G G G T A C T C A A
                550                 560                 570

170
Gly Lys Ile Val Asp Leu Val Lys Glu Leu
G G G A A A A T T G T G G A T T T G G T C A A G G A G C T T
                580                 590                 600
```

FIGURE 1E

```
           180
Asp Arg Asp Thr Val Phe Ala Leu Val Asn
GAC AGA GAC ACA GTT TTT GCT CTG GTG AAT
         610         620         630

190
Tyr Ile Phe Phe Lys Gly Lys Trp Glu Arg
TAC ATC TTC TTT AAA GGC AAA TGG GAG AGA
         640         650         660

200
Pro Phe Glu Val Lys Asp Thr Glu Glu Glu
CCC TTT GAA GTC AAG GAC ACC GAG GAA GAG
         670         680         690

210
Asp Phe His Val Asp Gln Val Thr Thr Val
GAC TTC CAC GTG GAC CAG GTG ACC ACC GTG
         700         710         720
```

FIGURE 1F

```
      220                                  230                                  240                                  250
Lys Val Pro Met Met Lys Arg Leu Gly Met    Phe Asn Ile Gln His Cys Lys Lys Leu Ser    Ser Trp Val Leu Leu Met Lys Tyr Leu Gly    Asn Ala Thr Ala Ile Phe Phe Leu Pro Asp
AAG GTG CCT ATG ATG AAG CGT TTA GGC ATG    TTT AAC ATC CAG CAT TGT AAG AAG CTG TCC    AGC TGG GTG CTG CTG ATG AAA TAC CTG GGC    AAT GCC ACC GCC ATC TTC TTC CTG CCT GAT
           730                750                     760                  780                     790                  810                     820                  840

```
        Glu Gly Lys Leu Gln His Leu Glu Asn Glu
        GAG GGG AAA CTA CAG CAC CTG GAA AAT GAA
        850             860             870
            260

Leu Thr His Asp Ile Ile Thr Lys Phe Leu
        CTC ACC CAC GAT ATC ATC ACC AAG TTC CTG
        880             890             900
            270

Glu Asn Glu Asp Arg Arg Ser Ala Ser Leu
        GAA AAT GAA GAC AGA AGG TCT GCC AGC TTA
        910             920             930
            280

His Leu Pro Lys Leu Ser Ile Thr Gly Thr
        CAT TTA CCC AAA CTG TCC ATT ACT GGA ACC
        940             950             960
            290
```

FIGURE 1H

```
                    300                              310                              320                              330
Tyr Asp Leu Lys Ser Val Leu Gly Gln Leu   Gly Ile Thr Lys Val Phe Ser Asn Gly Ala   Asp Leu Ser Gly Val Thr Glu Glu Ala Pro   Leu Lys Ser Leu Ala Val His Lys Ala
TAT GAT CTG AAG AGC GTC CTA GGT CAA CTG   GGC ATC ACT AAG GTC TTC AGC AAT GGG GCT   GAC CTC TCC GGG GTC ACA GAG GAG GCA CCC   CTG AAG CTC TCC AAG GCC GTG CAT AAG GCT
                    970                              1000                             1030                             1060
           980                   990              1010                   1020              1040                   1050              1070                   1080
```

FIGURE 1I

```
      340
Val Leu Thr Ile Asp Glu Lys Gly Thr Glu
GTG CTG ACC ATC GAC GAG AAA GGG ACT GAA
        1090         1100        1110

350
Ala Ala Gly Ala Met Phe Leu Glu Ala Ile
GCT GCT GGG GCC ATG TTT TTA GAG GCC ATA
        1120         1130        1140

360
Pro Met Ser Ile Arg Pro Glu Val Lys Phe
CCC ATG TCT ATC CGC CCC GAG GTC AAG TTC
        1150         1160        1170

370
Asn Lys Pro Phe Val Phe Leu Met Ile Glu
AAC AAA CCC TTT GTC TTC TTA ATG ATT GAA
        1180         1190        1200
```

FIGURE 1J

```
            380
Gln Asn Thr Lys Ser Pro Leu Phe Met Gly
CAA AAT ACC AAG TCT CCC CTC TTC ATG GGA
        1210        1220        1230
            390                 394
Lys Val Val Asn Pro Thr Gln Lys STOP
AAA GTG GTG AAT CCC ACC CAA AAA TAA CTG
        1240        1250
CCT CTC GCT CCT CAA CCC CCC CCC CCC C 3'
```

FIGURE 1K

DNA SEQUENCES EXPRESSING MAMMALIAN $\alpha_1$-ANTITRYPSIN

This application is a divisional of prior application Ser. No. 08/479,545 filed Jun. 7, 1995, now U.S. Pat. No. 5,736,379, which is a continuation of application Ser. No. 08/361,689 filed Dec. 22, 1994, now abandoned, which is a continuation of application Ser. No. 08/086,442 filed Jul. 2, 1993, now U.S. Pat. No. 5,399,684, which is a continuation of application Ser. No. 07/979,556 filed Nov. 18, 1992, now abandoned, which is a continuation of application Ser. No. 07/666,450 filed Mar. 11, 1991, now abandoned, which is a continuation of application Ser. No. 07/398,288 filed Aug. 22, 1989, now abandoned, which is a continuation of application Ser. No. 07/246,912 filed Sep. 16, 1988, now abandoned, which is a continuation of application Ser. No. 07/133,190 filed Dec. 15, 1987, now abandoned, which is a continuation of application Ser. No. 07/022,543 filed Mar. 3, 1987, now abandoned, which is a continuation of application Ser. No. 06/638,980 filed Feb. 7, 1984, now abandoned, which is a continuation of application Ser. No. 06/380,310 filed May 20, 1982, now abandoned.

BACKGROUND OF THE INVENTION

1. Field of the Invention $\alpha_1$-Antitrypsin is an important protease inhibitor present in mammalian blood. Its major physiological function appears to be the inhibition of neturophil elastase, a potent protease that hydrolyzes structural proteins. It also inhibits many other serine proteases.

A low level of $\alpha_1$-antitrypsin in the blood is often associated with chronic obstructive pulmonary emphysema and infantile liver cirrhosis. At present, more than 30 different genetic variants have been identified. Several of these are associated with low concentrations of the inhibitor in the blood.

The normal plasma level of $\alpha_1$-antitrypsin is about 2 mg/ml. Under most inflammatory conditions, an acute-phase response is initiated and the concentration of $\alpha_1$-antitrypsin is substantially increased. In order to study $\alpha_1$-antitrypsin deficiency at the molecular level and examine the mechanism of the acute phase response, it would be desirable to have pure $\alpha_1$-antitrypsin polypeptide. The $\alpha_1$-antitrypsin polypeptide could be used for the formation of antibodies to the numerous determinant sites to provide for detection of variants in the blood, as a ligand in assays for a $\alpha_1$-antitrypsin, and for introduction into a host having $\alpha_1$-antitrypsin deficiency.

2. Description of the Prior Art

Shochat, et al., J. Biol. Chem. (1978), 253:5630–5634; Morii, et al., J. Biochem. (1978), 83:269–277; Carrell, et al., Biochem. Biophys. Res. Commun. (1979), 91:1032–1037; Nega, et al., J. Biol. Chem. (1980), 255:4057–4061; and Crawford, Arch. Biochem. Biophys. (1973), 156:215–222; have resorted various characteristics of $\alpha_1$-antitrypsin. Kurachi, et al., PNAS (1981), 78:6826–6830, and Chandra, et al., Biochem. Biophys. Res. Comm. (1981), 103:751–758, describe cloning and sequencing of cDNA coding for $\alpha_1$-antitrypsin.

SUMMARY OF THE INVENTION

DNA sequences, including cDNA and rDNA capable of expressing mammalian $\alpha_1$-antitrypsin are provided, as well as compositions and methods for producing the polypeptide chain of $\alpha_1$-antitrypsin. $\alpha_1$-Antitrypsin polypeptide made by recombinant DNA is provided.

DESCRIPTION OF THE SPECIFIC CONDIMENTS

DNA sequences capable of expression of polypeptides having mammalian $\alpha_1$- antitrypsin biological activity are provided. The sequences can be used for introduction into a host cell to enhance the production of products having $\alpha_1$-antitrypsin activity. The DNA sequences include DNA sequences having exons and introns free of their normal flanking regions, messenger RNA which has been matured and is capped and includes a polyA 3' chain, cDNA obtained by transcribing mRNA and the combination of the DNA with DNA sequences, which provide regulatory signals for expression, replication, amplification, and regulated response to a variety of conditions and reagents.

The nucleic acid sequences and their expression products are polypeptides having $\alpha_1$-antitrypsin activity, in that the compounds inhibit elastase by forming an equimolar complex of the enzyme and the inhibitor with an association rate constant of greater than about $10^6$ per mole-sec. The compounds are derived from mammals, particularly primates, such as baboon and human. The chromosomal DNA fragment encoding $\alpha_1$-antitrypsin is less than about 10 kb, usually less than about 9 kb. The approximate sizes of the exon regions I, II, III, and IV are, respectively, about 0.71, 0.33, 0.13, and 0.2 kb's in length. The sizes of the introns A, B, and C are, respectively, about 1.45, 1.15, and 0.8 kb's, and the three introns are generally located within the 5' half of the DNA. The cDNA encoding $\alpha_1$-antitrypsin is about 1.182 kb's in length. The mature mRNA en coding human $\alpha_1$-antitrypsin is about 1.4 kb's in length.

The DNA sequences may be used in a variety of ways. Where chromosomal DNA is employed for transformation of host cells which are capable of recognizing the intron borders and providing for the mature mRNA, the DNA may be calcium precipitated in accordance with conventional ways and used for transformation of primate cells. For the most part, cells which can grow in vitro are cancerous and various cancerous lines may be employed for transformation. Particularly, cells of hepatic origin; e.g., hepatomas, may be employed. One may then select for transformed cells overproducing $\alpha_1$-antitrypsin.

Rather than using bare DNA, cDNA obtained by reverse transcription of mature mRNA may be inserted into a wide variety of vectors for introduction into a host for expression of $\alpha_1$-antitrypsin. The particular vector will depend upon the host and other considerations affecting the efficiency of production of the $\alpha_1$-antitrypsin. Hosts which may be employed for the production of $\alpha_1$-antitrypsin include unicellular microorganisms, such as the prokaryotes, bacteria, and eukaryotes, such as fungi, e.g., yeast, algae, protozoa, and the like. Vectors are available for cloning, expression, for amplification of genes, as well as providing for external controls, such as temperature, heavy metal ions, or the like.

Methods of introducing DNA into an organism and providing for amplification of genes encoded into such DNA may be found in PCT International Application Nos. US 81/00239 and US 81/00240. The choice of vector, regulatory signals, or other control systems will be primarily a matter relating to convenience, availability, fermentation equipment, economics, and intended use of the product. The aforementioned PCT patents provided for a generalized description of hybrid DNA technology, which technology is incorporated herein by reference.

The primate gene for $\alpha_1$-antitrypsin can be obtained by instituting hepatic local inflammation in a primate, then sacrificing the primate and isolating the liver. Polysomes are then obtained as described in the literature, and the polysomes synthesizing nascent $\alpha_1$-antitrypsin enriched by immunopreipitation. After analysis by mRNA-dependent cell-free translation employing reticulocyte, the desired cDNA would be obtained from the mRNA.-enriched preparation. The CDNA is then restriction mapped and superfluous sequences removed or the cDNA is tailed, for example, a polydG-polydC tail, and then inserted into the cohesive ends of a vector. Based on the sequences, the CDNA may be modified in a variety of ways. Superfluous nucleotides, not involved in coding for $\alpha_1$-antitrypsin, may be removed by primer repair. See, for example, Goeddel, et al., Nucl. Acids Res. (1980), 8:4057–4074; Razin, et al., PNAS USA (1978), 75:4268–4270; and Wallace, et al., Science (1980), 209:1396–1400.

For primer repair, a synthetic single-stranded DNA oligomer is prepared which is complimentary to the 3'-terminus of the coding ("sense") strand of the gene encoding the $\alpha_1$-antitrypsin. The cDNA is denatured and the DNA oligomer hybridized to the coding strand. The hybrid is then treated with T4 DNA polymerase or E coli DNA polymerase large ("Klenow") fragment, so that a double strand is obtained where the coding strand has the ATG codon as the initial 3 nucleotides.

Alternatively, instead of including the leader sequence, one may use in vitro nutagenesis and prepare a synthetic DNA oligomer which replaces the Ala codon at −1 with the Met codon ATG. As the first step in this process, one would prepare a synthetic DNA oligomer, including at least the following sequence: GACTAGCTC, normally having not more than about six more nucleotides at the 5' end and at least about three nucleotides at the 3' end of the oligomer complimentary to the nucleotide of the coding strand of the $\alpha_1$-antitrypsin gene. After hybridizing the coding strand with the oligomer, the mismatched hybrid will then be treated with the same polymerase indicated above, so that the resulting double-stranded DNA would have a blunt-end terminus beginning with the nucleotides of the oligomer. In this way, the resulting dsDNA could be inserted into an expression vector, downstream from an appropriate promoter, and ribsomal start site, so that expression would be initiated at the synthetically created Met codon. As appropriate, linkers may be used to provide for cohesive ends or, alternatively, the DNA sequence may be blunt end ligated into the expression vector.

An alternative method would be to cleave the DNA fragment containing the sequence encoding for $\alpha_1$-antitrypsin intact and then, by employing an exonuclease, such as Bal 31, and by chewing back the terminal residues, one obtains a heterogeneous mixture of fragments. By timing the digestion, based on the number of nucleotides which must be removed, one can obtain fragments which will have the ATG codon in appropriate juxtaposition with a ribosomal start site, when such fragments are inserted into an expression vector. Initially, one may introduce the fragments into a cloning vector and, by employing appropriate probes, select for the clone having the desired fragments.

A preferred way is to follow the procedure of Heitzman et al., Nature (1981) 293:717–722, which disclosure is incorporated herein by reference. By restricting with BamHI, an intact fragment encoding for $\alpha_1$-antitrypsin is obtained except for the first two codons encoding Met and Glu. By ligating a linker having the nucleotides encoding the amino acids to the $\alpha_1$-antitrypsin frament, the entire $\alpha_1$-antitrypsin sequence may be inserted into an expression vector for expression.

In expressing the $\alpha_1$-antitrypsin, one may retain the leader sequence or remove the leader sequence, depending upon the host. Where a higher order host is employed and the leader peptide is retained, the host secretes the $\alpha_1$-antitrypsin with removal of the leader peptide.

Various vectors may be employed, such as plasmids, cosmids, or viruses. The expression vectors may conveniently be shuttle vectors, which allow for amplification in a prokaryote with expression in a eukaryote. Therefore, one would require replicons for both eukaryotes and prokaryotes in the vector. Secondly, one can provide for a wide variety of markers, such as cytotoxic resistance, viral immunity, prototrophy in an auxotrophic host, and the like. Conveniently, antibiotic resistance can be employed as a useful marker. Other features of the vector may include homologous sequences with the host gene to provide for integration of the $\alpha_1$-antitrypsin gene into the chromosome of the host. If desired, minichromosomes may be employed as described by Clarke and Carbon, PNAS USA (1980), 77:2173–2177; and Clarke and Carbon, Nature (1980), 287(5782):504–509.

Figure 1A:
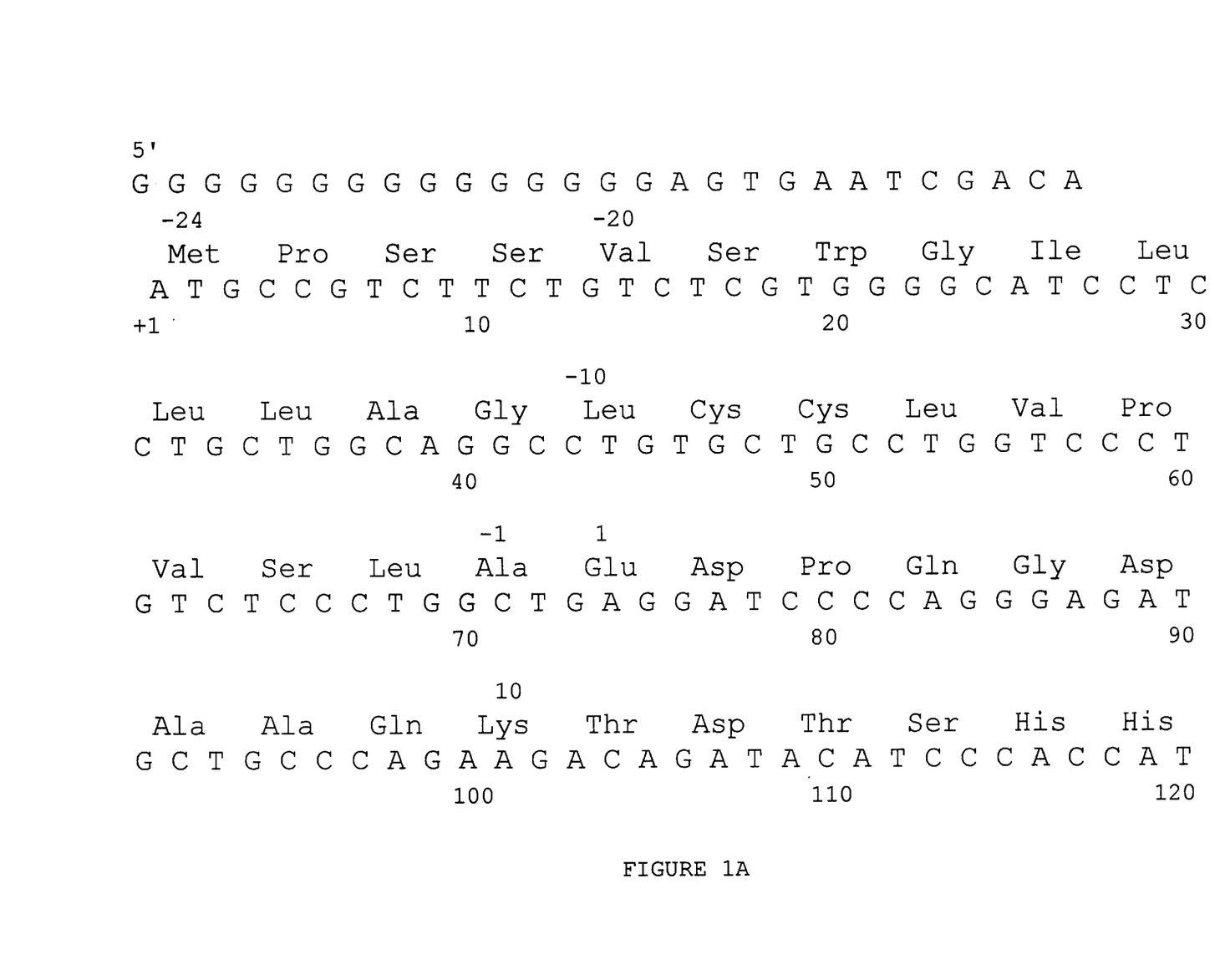
FIGS. 1A–1K set forth the human $\alpha_1$-antitrypsin cDNA discussed in the specification.
Figure 1B:
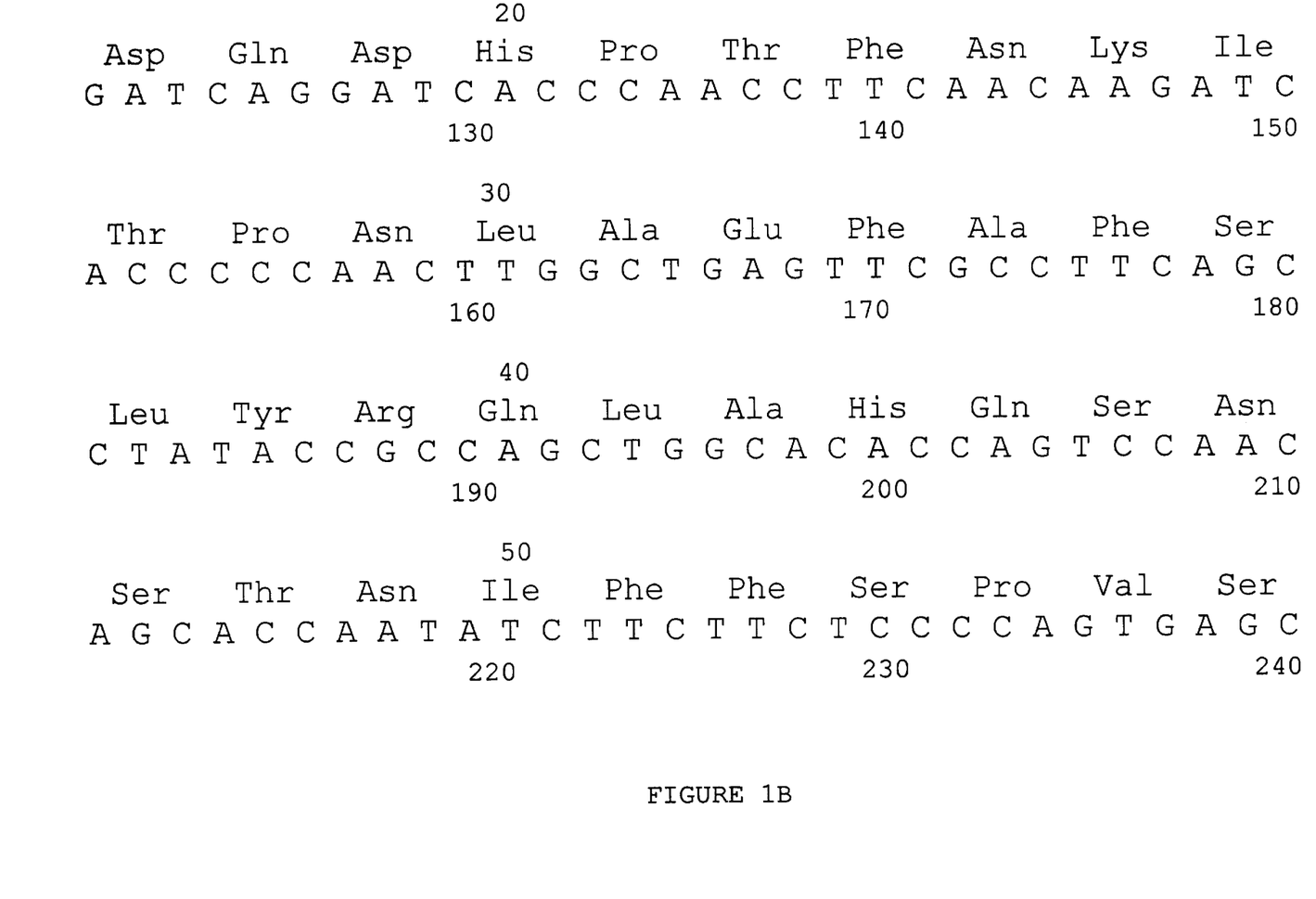
Figure 1C:
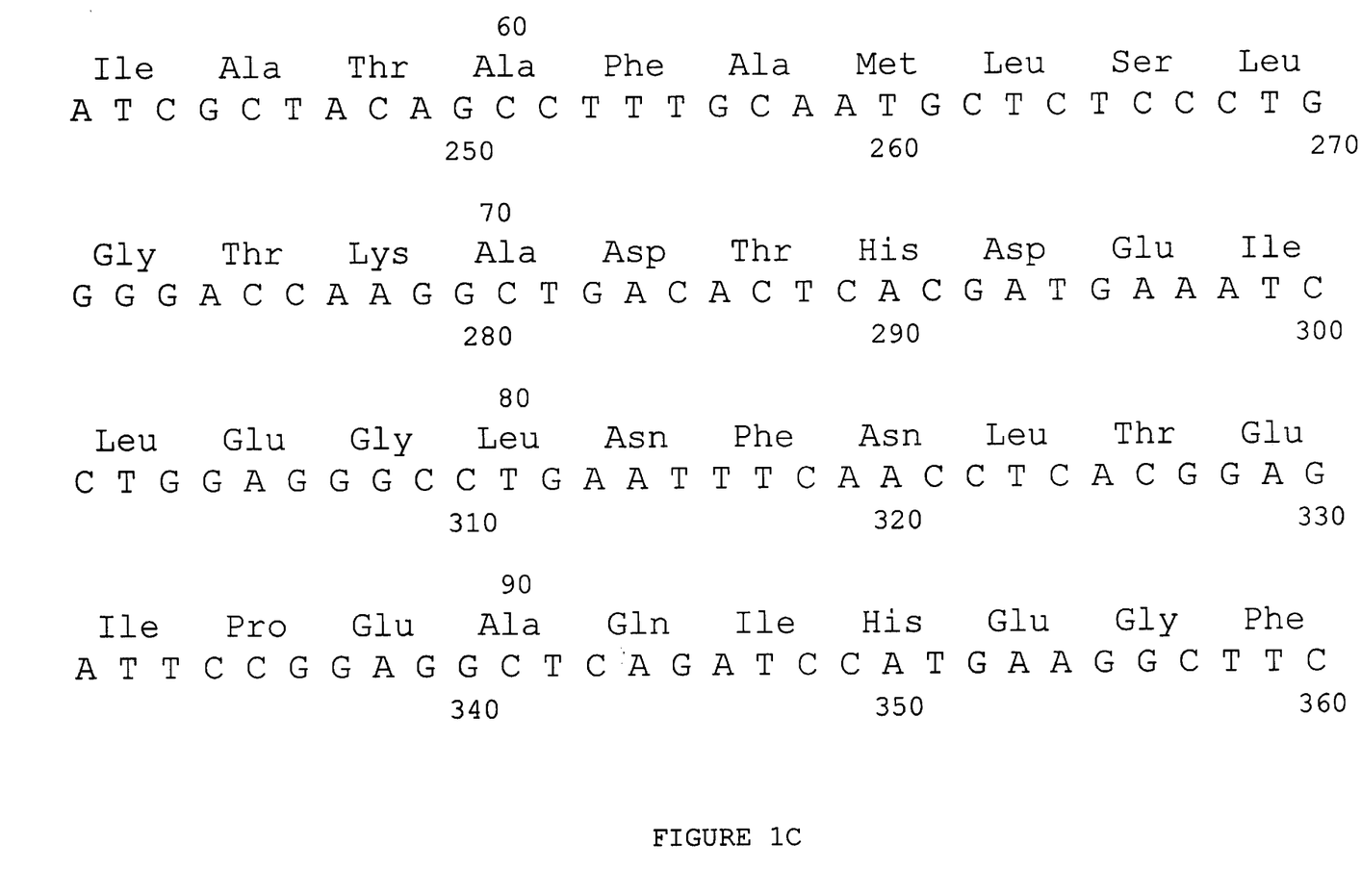
Figure 1D:
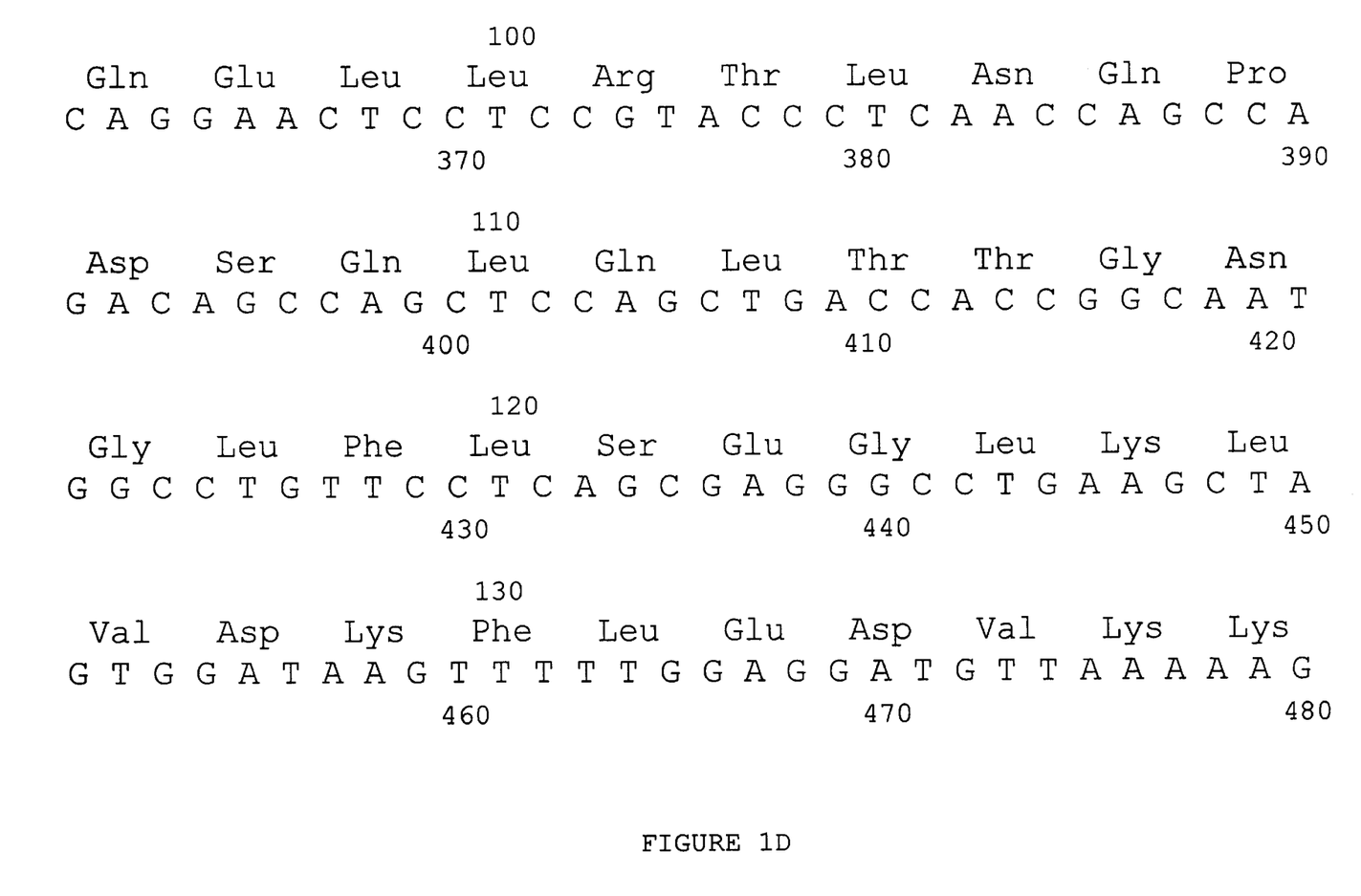
Figure 1E:
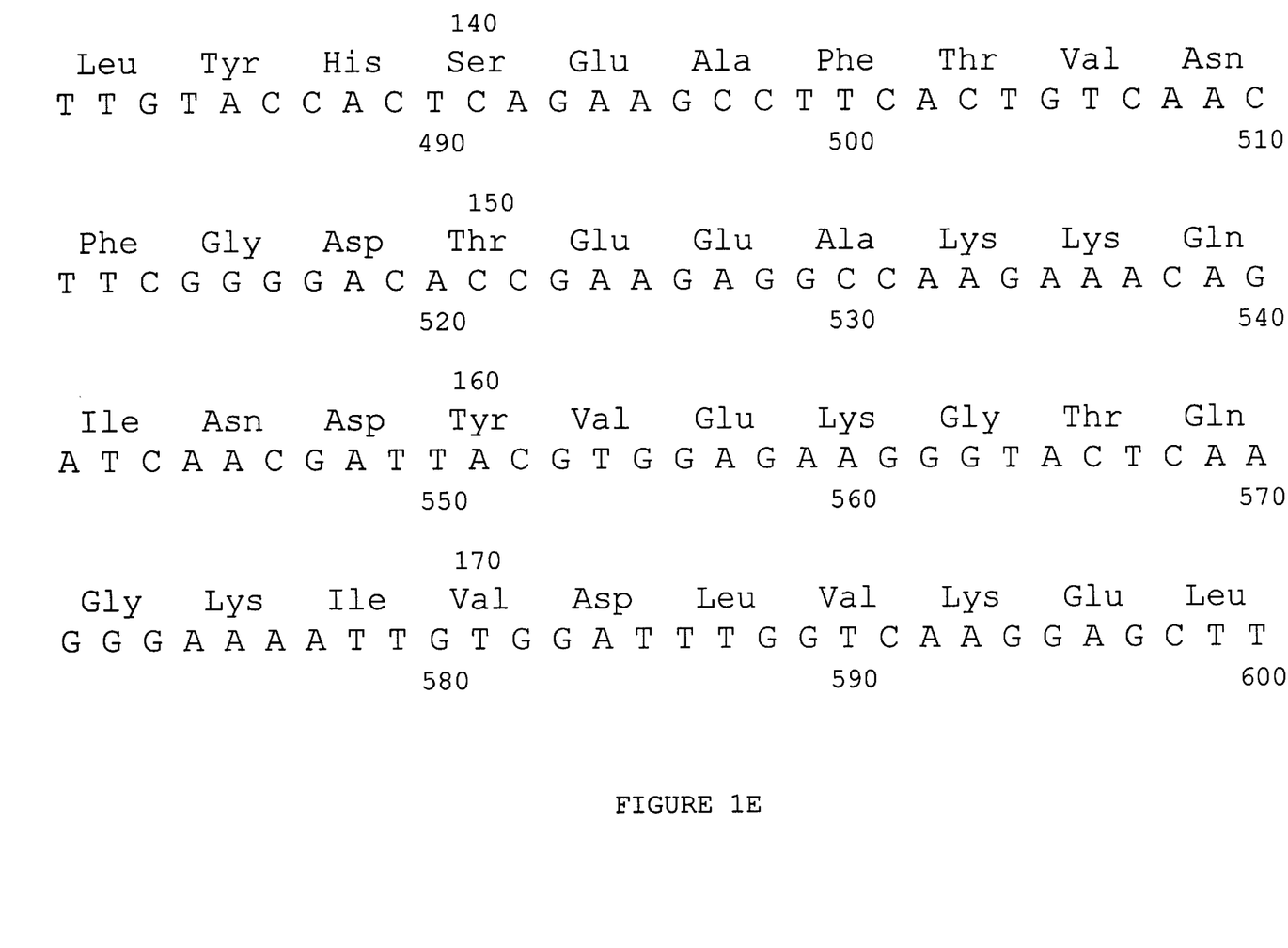
Figure 1F:
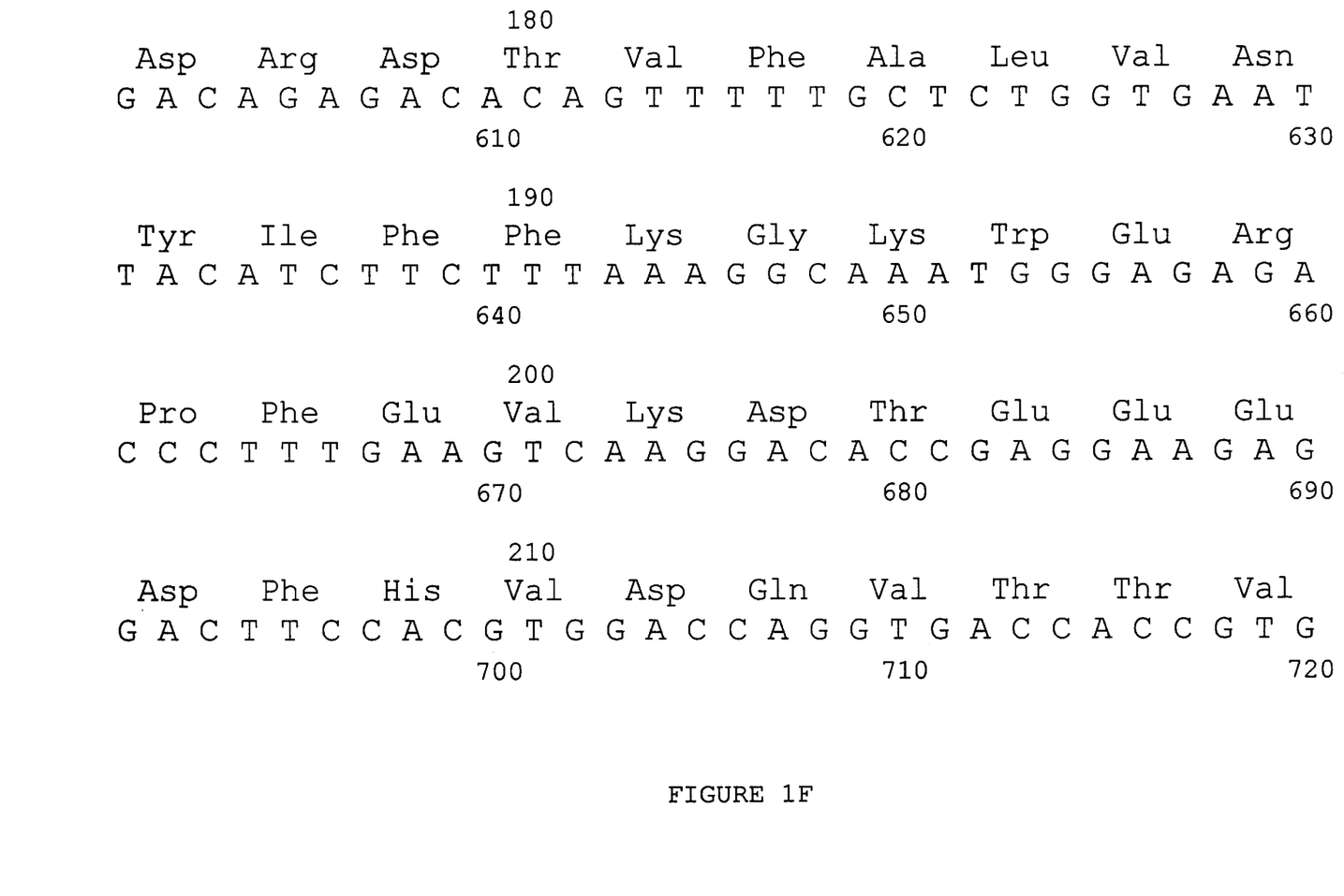
Figure 1G:
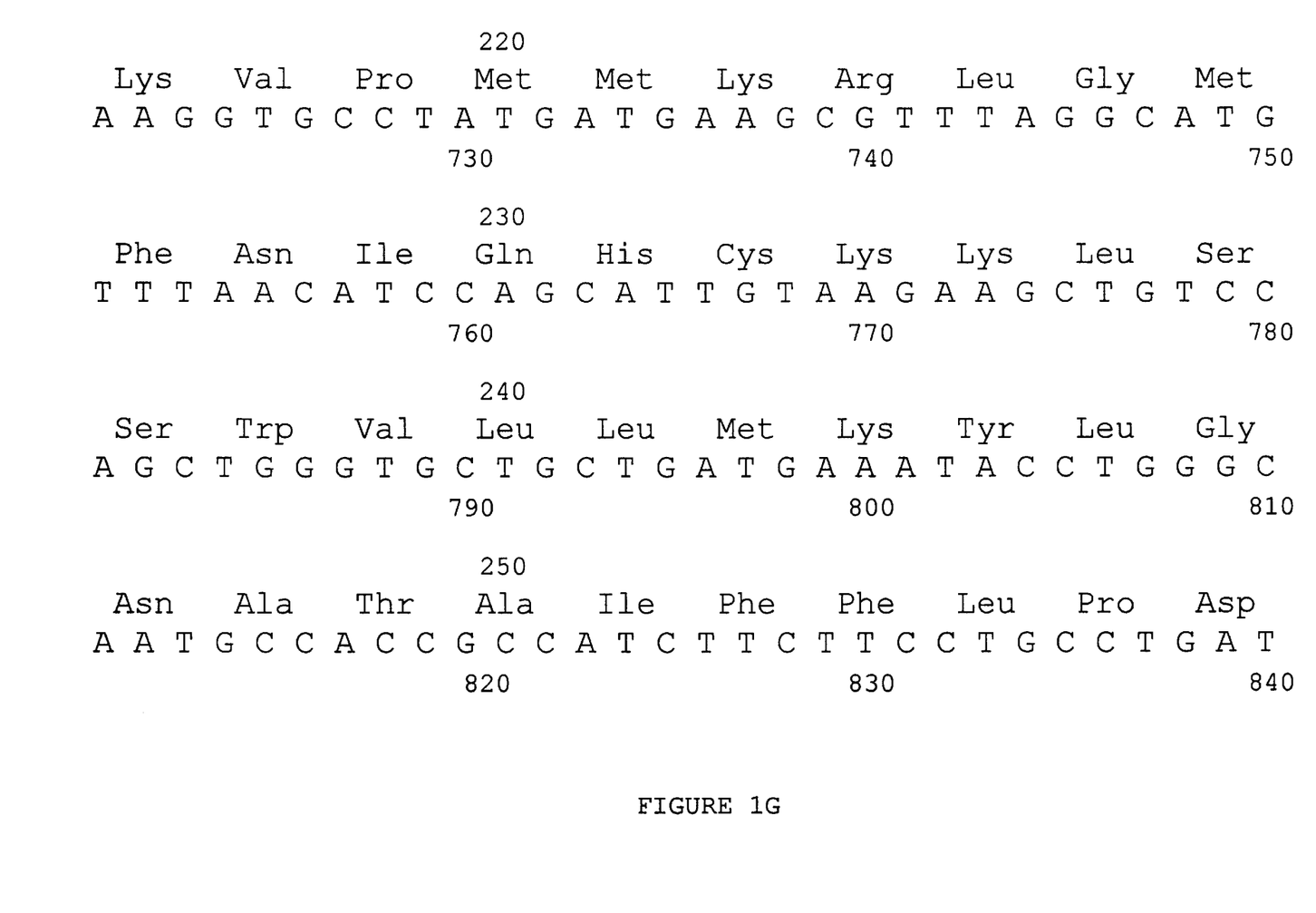
Figure 1H:
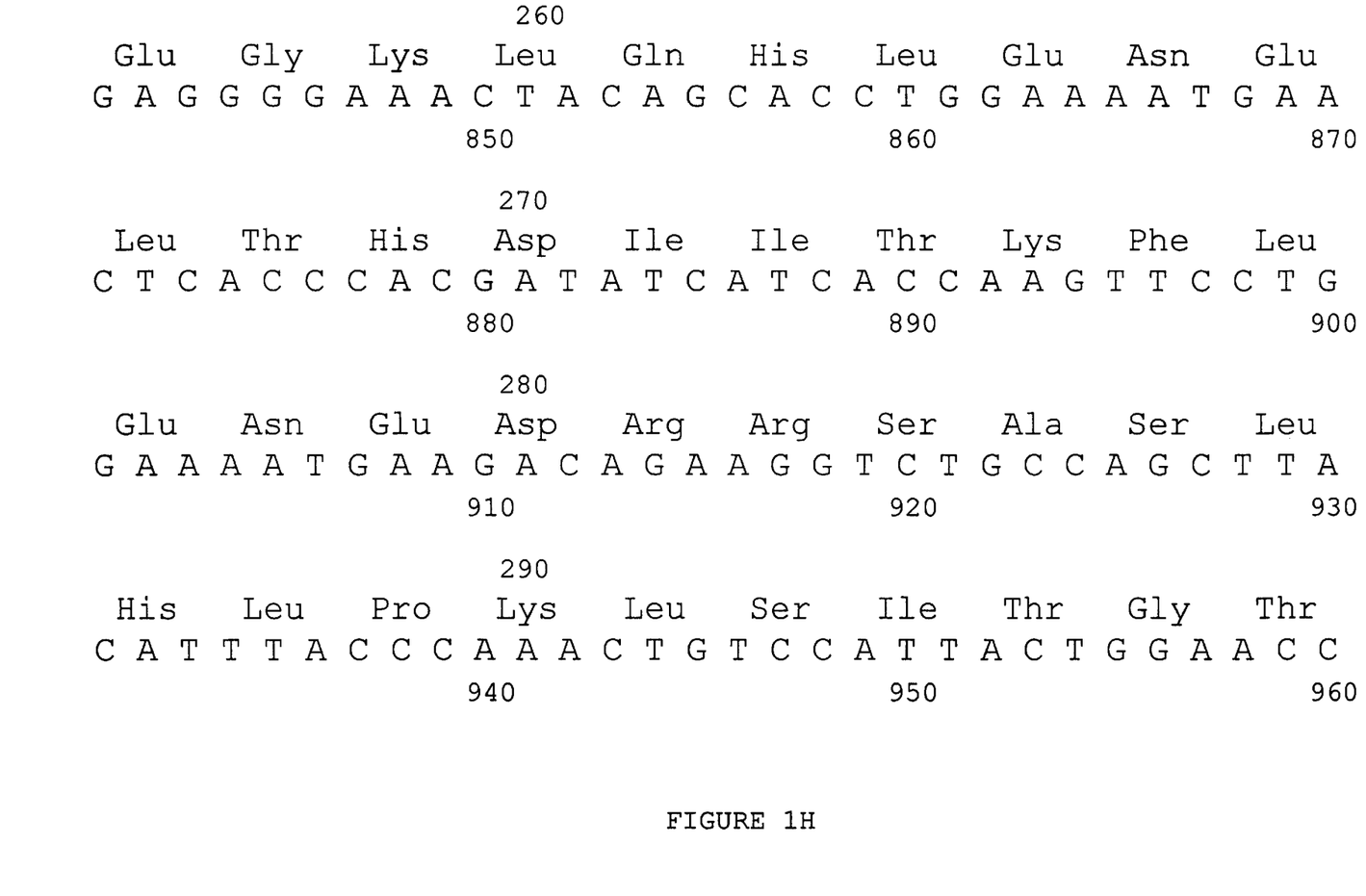
Figure 1I:
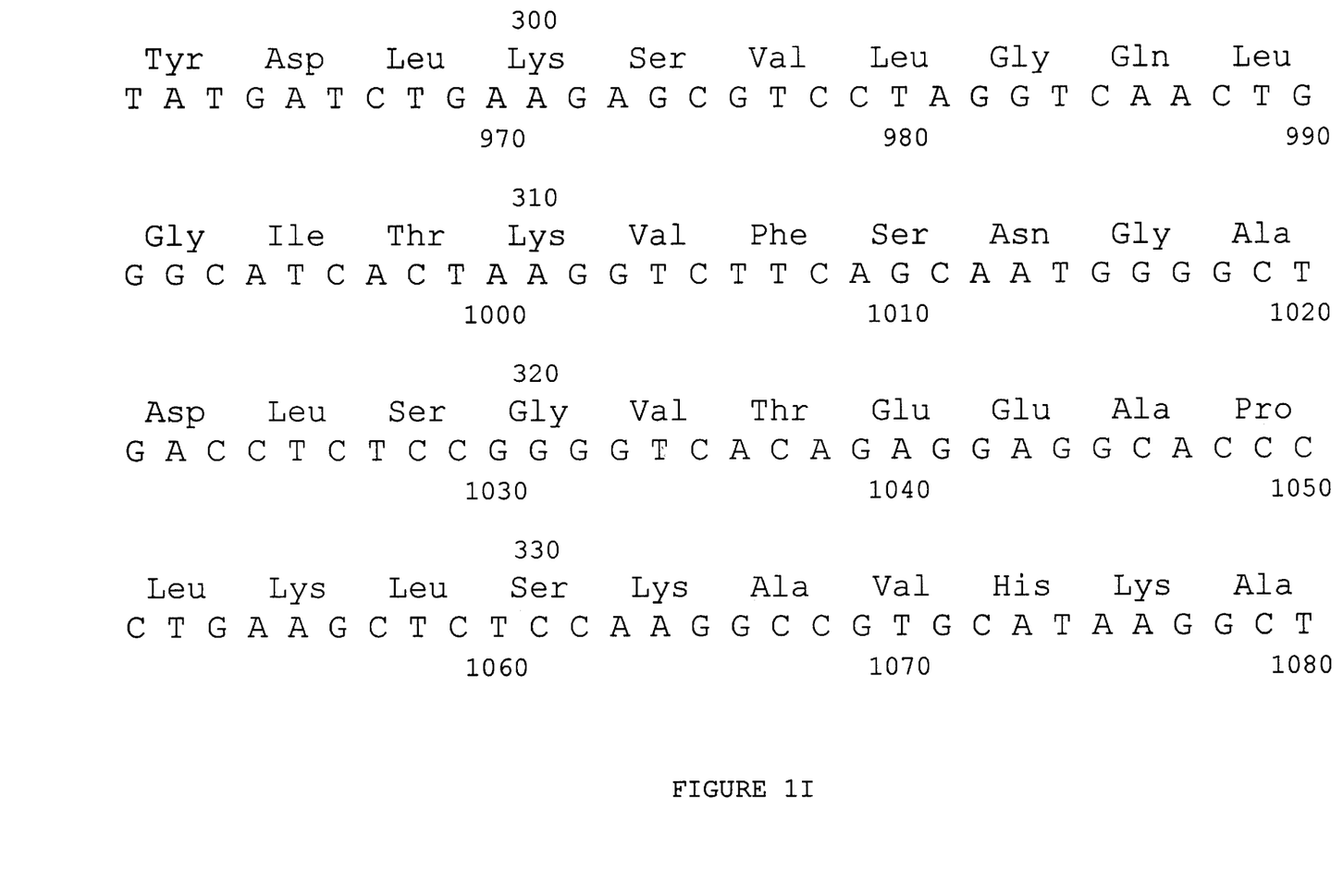
Figure 1J:
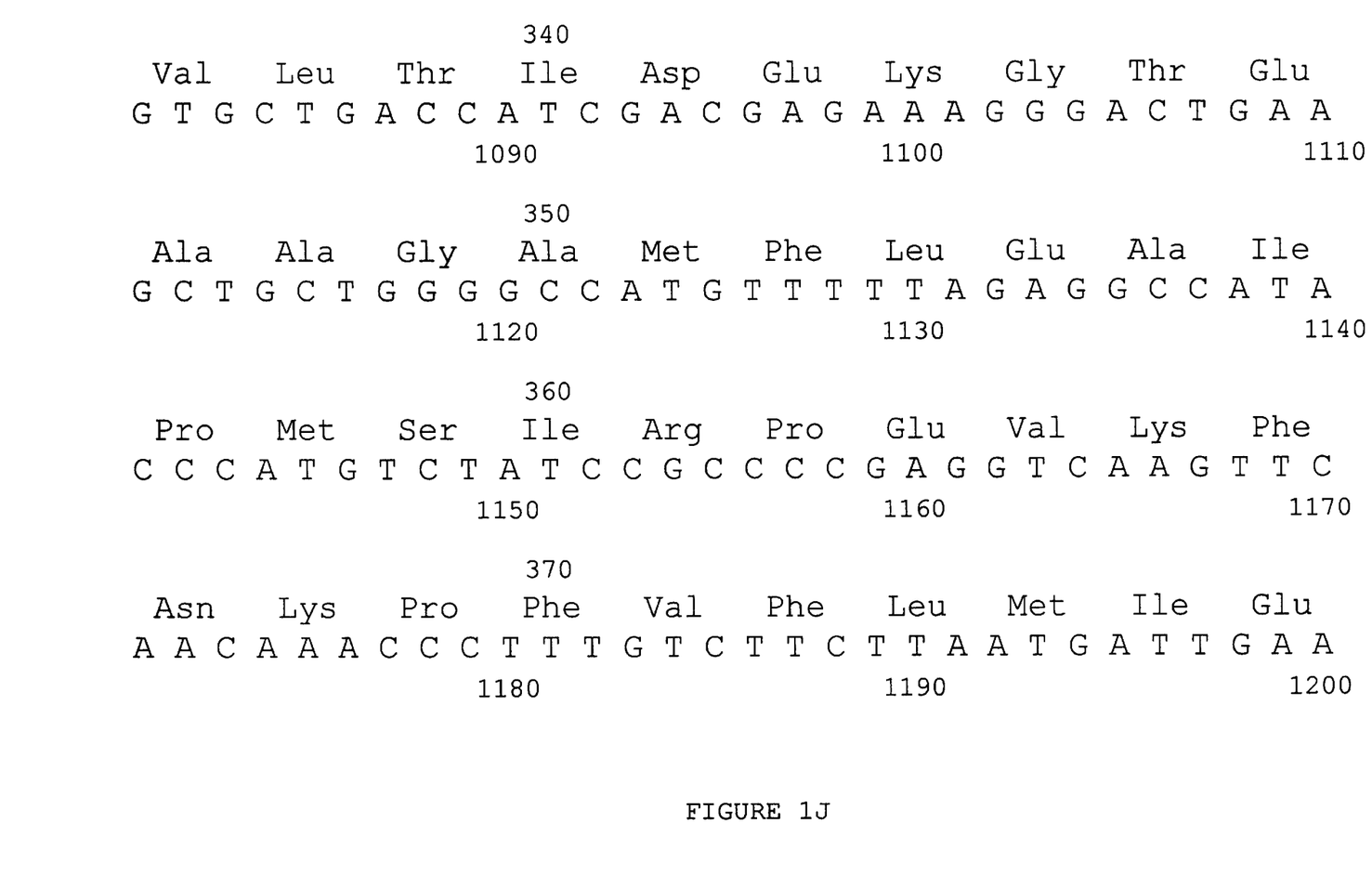
Figure 1K:
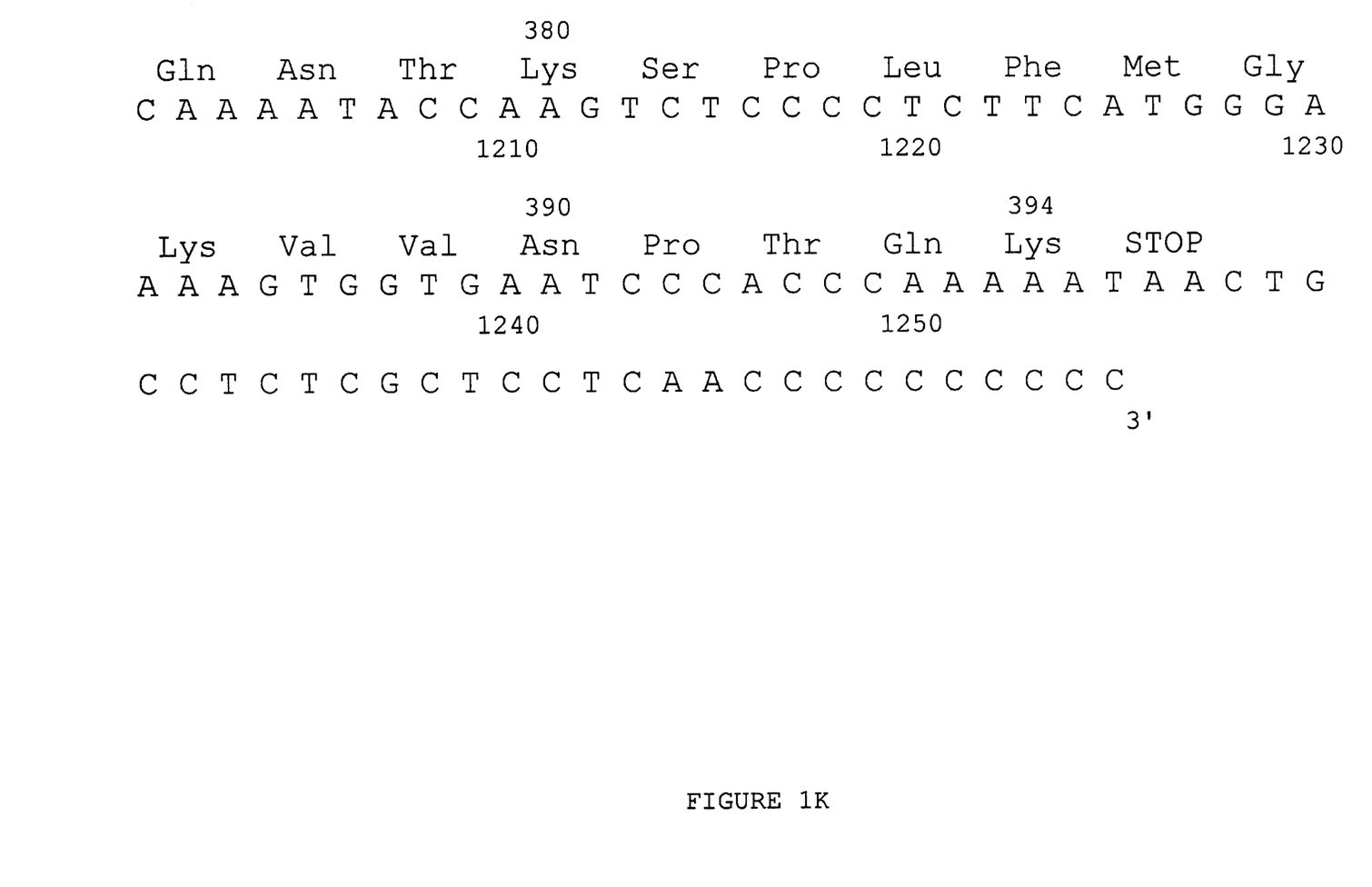

The human $\alpha_1$antitrypsin cDNA is set forth in the FIGS. 1A–1K.

The gene for the human $\alpha_1$-antitrypsin is of about 5 kd. The nucleotide coding for the $\alpha_1$-antitrypsin, including the f-Met codon and leader sequence, is 1254 nucleotides, which includes 72 nucleotides involved with the leader sequence, as compared with about 1400 nucleotides for the mature messenger RNA. The mature human $\alpha_1$-antitrypsin has 394 amino acids, as set forth in the prior sequence.

In order to describe the manner in which the DNA sequence for human a $\alpha_1$-antitrypsin and baboon $\alpha_1$-antitrypsin were developed, the following examples are offered by way of illustration and not by way of limitation.

Experimental

Overlapping Genomic $\alpha_1$-Antitrypsin Clones

A total of 16 independent phage isolates were obtained when 2×10 6 plaques from the human genomic DNA library (Lawn, et al., Cell (1978), 15:1156–1174) were screened using the baboon $\alpha_1$-antitrypsin cDNA clone (Chandra, et al., Biochem. Biophys. Res. Comm. (1981), 103:751–758) as a hybridization probe. Subsequent analysis of the 16 isolates indicated that they originated from four independent clones. The four clones, labeled aAT135, aAT35, aAT80 and aAT101, were analyzed by restriction mapping and Southern hybridization using as probes an Mbo II fragment of pbaαlal DNA, which contains the 3' terminal region of the baboon cDNA (Chandra, et al., ibid.) and an Hha I fragment of pBAαla2 DNA which is a baboon cDNA clone lacking only about 100 nucleotides at the 5' end of the mRNA (Kurachi, et al., PNAS USA (1981), 78:6826–6830). These results have established the orientation of the human $\alpha_1$-antitrypsin gene and have indicated that the entire gene may reside within a 9.6 kb Eco RI DNA fragment in the human genome.

Mosaic Structure of the Human $\alpha_1$Antitrypsin Gene

The overall structure of the human $\alpha_1$-antitrypsin gene was established by electron microscopic examination of hybrid molecules formed between the cloned chromsomal DNA and baboon $\alpha_1$-antitrypsin mRNA. The mature mRNA consists of approximately 1400 nucleotides. DNA was denatured thermally and hybrids were formed subsequently under conditions that favored RNA/DNA hybridization but not DNA/DNA reassociation. From the electron micrographs and line drawings, it was evident that there are three intervening DNA loops (introns) of various sizes within the human $\alpha_1$-antitrypsin gene. The poly(A) tract in the mRNA was clearly visible in the hybrid molecule, thereby confirming the orientation of the gene. When aAT135 DNA was cleaved with Eco RI prior to hybrid formation with the baboon mRNA, the smallest intervening DNA loop was very close to one end of the DNA molecule. Numonic measurements of the hybrid molecules have indicated that the approximate sizes of exon regions I, II, III, and IV are 0.71, 0.33, 0.13 and 0.27 kb's in length, respectively. The sizes of introns A, B, and C are 1.45, 1.15, and C0.8 kb's, respectively, and all three introns appear to be located within the 3' half of the mRNA.

In order to characterize the human chromosomal $\alpha_1$-antitrypsin gene in greater detail, the 9.6 kb Eco RI DNA fragment was subcloned into the Eco RI site of pBR322. The resulting clone, pAT9.6, was analyzed by restriction mapping and Southern hybridization. Four exon segments were identified within the 9.6 kb Eco RI DNA fragment using a combination of enzymes that do not cut the baboon $\alpha_1$-antitrypsin CDNA insert in pBa$\alpha$la2 (Kurachi, et al. (1981), supra) These results confirmed the existence of three introns in the human $\alpha_1$-antitrypsin gene. The presence of only three introns in the peptide-coding region of the human chromodomal $\alpha_1$-antitrypsin gene was confirmed by DNA sequence analysis.

The 5' and 3' terminal sequences of the human $\alpha_1$-antitrypsin gene

Southern hybridization analysis between different portions of the baboon cDNA clone and human geonomic fragments generated by digestion of pAT9.6 revealed DNA fragments which hybridize uniquely with$^2$either the 5' or the 3' end of the cDNA probe. By DNA sequencing, fragments of the human genomic DTA that code for amino acids at both the amino and carboxyl-terminal regions of human $\alpha_1$-antitrypsin were identified. The distance between these two regions is approximately 5 kb, which is in good agreement with our estimates of the size of the gene, based on the electron micrographs. The amino acid sequence at the amino-terminal region agrees for 30 of the 33 residues that have been published for human $\alpha_1$-antitrypsin (Morii et al., J. Biochem. (1978) 83:269–277). Amino acids that are different include $Lys_{10}$, $His_{20}$ and $Ile_{26}$, which were reported as Glu, Ser and Leu, respectively. The DNA sequence corresponding to the amino-terminal region of the protein was confirmed by sequencing both strands of the geonimi DNAj. Furthermore, the residues in question are identical to those determined for baboon $\alpha_1$-antitrypsin. The amino acid sequence containing 32 residues at the carboxyl end of the mature protein was also deduced from the genomic DNA sequence. This amino acid sequence is in complete agreement with that previously published for $\alpha_1$-antitrypsin (Carrell et al., Biochem, Biophys. Res. Comm. (1979) 91:1032–1037). Also, the genomic DNA sequence was identical with the corresponding nucleotide sequence of a human $\alpha_1$-antitrypsin cDNA clone.

The first ATG start codon at the 5' end of the $\alpha_1$-antitrypsin gene is located 24 amino acids upstream from the amino-terminal Glu residue in the mature protein. This region appears to code for a typical signal peptide, which is removed from the mature protein during intracellular processing prior to extracellular transport. The features of this signal peptide are similar to those seen for other signal peptides including an amino terminal methionine residue, a hydrophobic core flanked by regions of more polar residues, a small uncharged amino acid at the putative cleavage site, proline at position −5 and a length of ~15–30 amino acid residues. Furthermore, there appears to be a "TATA box" sequence located at position −25 to −31 of the gene, which resembles the consensus sequence, $TATA_{ATA}^{TAT}$, proposed by Cordon et al. The transcription start point in eukaryotes also has a consensus sequence, PyCAPyPyPyPyPy (A=position+1; Py represents pyrimidine.

Based on the description in Kurachi et al, (1981), supra, the baboon $\alpha_1$-antitrypsin gene can also be used for producing baboon $\alpha_1$-antitrypsin as described above in conjunction with the disclosure of Kurachi.

In accordance with the subject invention, $\alpha_1$-antitrypsin can be produced by hybrid DNA techniques. By virtue of the flexibility of hybrid DNA technology, large amounts of $\alpha_1$-antitrypsin free of sugar substituents can be obtained. Furthermore, by employing appropriate hosts, the presence of the leader peptide allows for secretion of the product into the nutrient medium for ease of isolation.

Although the foregoing invention has been described in some detail by way of illustration and example for purposes of clarity of understanding, it will be obvious that certain changes and modifications may be practiced within the scope of the appended claims.

What is claimed is:

1. A method for preparing $\alpha_1$-antitrypsin which comprises introducing into a host cell a vector comprising a mammalian $\alpha_1$-antitrypsin, DNA sequence that hybridizes to the human $\alpha_1$-antitrypsin cDNA shown in FIGS. 1A–1K or its complement and which encodes a polypeptide exhibiting $\alpha_1$-antitrypsin activity, where said vector is compatible with said host cell and replicates in said host cell;

growing said host cell whereby said $\alpha_1$-antitrypsin is expressed; and isolating said $\alpha_1$-antitrypsin.

2. A method according to claim 1, wherein said $\alpha_1$antitrypsin is human $\alpha_1$-antitrypsin.

* * * * *

UNITED STATES PATENT AND TRADEMARK OFFICE
CERTIFICATE OF CORRECTION

PATENT NO. : 6,025,161
DATED : February 15, 2000
INVENTOR(S) : E.W. Davie et al.

It is certified that error appears in the above-identified patent and that said Letters Patent is hereby corrected as shown below:

| COLUMN | LINE | | |
|---|---|---|---|
| [62] Pg. 1, col. 1 | Related U.S. Applications, line 3 | "Nov. 22" should read --Dec. 22-- | |
| [62] Pg. 1, col. 1 | Related U.S. Applications, line 16 | "06/380,810" should read --06/380,310-- | |
| [56] Pg. 1, col. 1 | Refs. Cited (Other Publs., Item 2) | "78:6617," should read --78:6613-6617,-- | |
| [56] Pg. 1, col. 1 | Refs. Cited (Other Publs., Item 4) | "a lpha" should read --alpha-- | |
| [56] Pg. 1, col. 1 | Refs. Cited (Other Publs., Item 5) | "(1982." should read --(1982) abstract-- | |
| [56] Pg. 1, col. 2 | Refs. Cited (Other Publs., Item 6) | "primer"," should read --primers",-- | |

UNITED STATES PATENT AND TRADEMARK OFFICE
CERTIFICATE OF CORRECTION

PATENT NO. : 6,025,161
DATED : February 15, 2000
INVENTOR(S) : E.W. Davie et al.

It is certified that error appears in the above-identified patent and that said Letters Patent is hereby corrected as shown below:

COLUMN    LINE

| COLUMN | LINE | |
|---|---|---|
| [56]<br>Pg. 1, col. 2 | Refs. Cited<br>(Other Publs.,<br>Item 16) | "$\alpha_{1\text{-}antitrypsin\ gene.}$" should read --$\alpha_1$-antitrypsin gene."-- |
| [56]<br>Pg. 2, col. 1 | Refs. Cited<br>(Other Publs.,<br>Item 20) | "$\alpha_1$antitrypsin" should read --$\alpha_1$-antitrypsin-- |
| 1 | 56 | "resorted" should read --reported-- |
| 2 | 5 | "CONDIMENTS" should read --EMBODIMENTS-- |
| 3 | 8 | after "mRNA" delete "." |
| 3 | 9 | "CDNA" should read --cDNA-- |
| 3 | 12 | "CDNA" should read --cDNA-- |
| 4 | 26 | before "FIGS." delete "the" |
| 4 | 36 | after "human" delete "a" |
| 4 | 50 | "pba$\alpha$1a1" should read --pBa$\alpha$1a1-- |
| 4 | 59 | "$\alpha$1Antitrypsin" should read --$\alpha$1-Antitrypsin-- |

UNITED STATES PATENT AND TRADEMARK OFFICE
CERTIFICATE OF CORRECTION

PATENT NO. : 6,025,161
DATED : February 15, 2000
INVENTOR(S) : E.W. Davie et al.

It is certified that error appears in the above-identified patent and that said Letters Patent is hereby corrected as shown below:

| COLUMN | LINE | |
|---|---|---|
| 5 | 12 | "C0.8" should read --0.8-- |
| 5 | 22 | "CDNA" should read --cDNA-- |
| 6 (Claim 1, | 42 line 3) | after "$\alpha_1$-antitrypsin" delete "," |

Signed and Sealed this

Twenty-fourth Day of April, 2001

Attest:

NICHOLAS P. GODICI

Attesting Officer

Acting Director of the United States Patent and Trademark Office